United States Patent [19]

Rackur et al.

[11] 4,305,952
[45] Dec. 15, 1981

[54] 8-ARYL-5,6,7,8-TETRAHYDROPYRAZOLO(3,4-b)(1,4)-DIAZEPINE-1H, 4H-5,7-DIONES, AND MEDICAMENTS CONTAINING THESE

[75] Inventors: Gerhard Rackur, Kelkheim; Irmgard Hoffmann, Bad Soden am Taunis, both of Fed. Rep. of Germany

[73] Assignee: Hoechst Aktiengesellschaft, Frankfurt am Main, Fed. Rep. of Germany

[21] Appl. No.: 122,692

[22] Filed: Feb. 19, 1980

[30] Foreign Application Priority Data

Feb. 20, 1979 [DE] Fed. Rep. of Germany ....... 2906401

[51] Int. Cl.$^3$ ..................... A61K 31/55; C07D 487/04
[52] U.S. Cl. ......................... 424/273 P; 260/239.3 B; 260/163; 548/362; 548/358; 546/279
[58] Field of Search ................. 260/239.3 B; 548/370; 424/273 P

[56] References Cited

U.S. PATENT DOCUMENTS 3,700,657 10/1972 Nordin ..................... 260/2 39.3 B
3,984,398 10/1976 Rossi ........................... 260/239.3 B

FOREIGN PATENT DOCUMENTS 2360852 6/1974 Fed. Rep. of Germany .

OTHER PUBLICATIONS

Chem. Abst., 1977, vol. 86, p. 4510cs.
Nomenclature of Organic Chemistry, p. 64, Butterworths, London, 1969.
Affane-Nguema et al., J. Het. Chem., 1977, vol. 14(6), pp. 1013-1019.

*Primary Examiner*—John M. Ford
*Assistant Examiner*—Natalia Harkaway
*Attorney, Agent, or Firm*—Curtis, Morris & Safford

[57] ABSTRACT

8-Aryl-5,6,7,8-tetrahydropyrazolo(3,4-b)(1,4)diazepine-1H,4H-5,7-diones of the formula

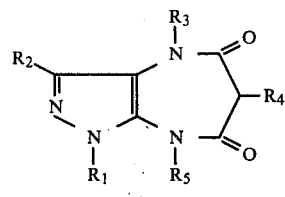

in which $R_1$ through $R_5$ are as defined in the specification, and medicaments containing these having an anxiolytic action.

6 Claims, No Drawings

8-ARYL-5,6,7,8-TETRAHYDROPYRAZOLO(3,4-B)(1,4)-DIAZEPINE-1H, 4H-5,7-DIONES, AND MEDICAMENTS CONTAINING THESE

The invention provides 8-aryl-5,6,7,8-tetrahydropyrazolo(3,4-b) (1,4)-diazepine-1H,4H-5,7-diones of the formula

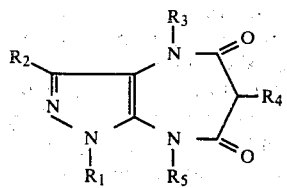

in which
- $R_1$ and $R_2$ are identical or different and represent each a hydrogen atom, an alkyl group having from 1 to 6 carbon atoms, one of the radicals $R_1$ or $R_2$ possibly being a benzyl or phenyl group;
- $R_3$ is a hydrogen atom, an alkyl group having from 1 to 6 carbon atoms, optionally being substituted by an alkoxy group having from 1 to 6 carbon atoms or a dialkylamino group having from 2 to 12 carbon atoms or a cycloalkyl group having from 3 to 6 carbon atoms, or an alkenyl or alkinyl group having from 2 to 6 carbon atoms, a cycloalkyl group having from 3 to 6 carbon atoms, or a carbalkoxy group having from 2 to 6 carbon atoms;
- $R_4$ is a hydrogen atom, an alkyl group having from 1 to 6 carbon atoms, a phenyl group, a hydroxy group, an alkoxy group having from 1 to 6 carbon atoms, a carbalkoxy group having from 2 to 6 carbon atoms, an acyl group having from 2 to 6 carbon atoms, an amino group, an alkylamino group having from 1 to 7 carbon atoms, or a dialkylamino group having from 2 to 12 carbon atoms or a carbamoyl group carrying an amino group, an alkylamino group having from 1 to 6 carbon atoms or a dialkylamino group having from 2 to 12 carbon atoms;
- $R_5$ is a phenyl group, a phenyl group being mono- or bisubstituted by methyl, Cl, Br, F, nitro, cyano and/or trifluoromethyl, or a 2-pyridyl group.

The invention relates especially to compounds in which $R_1$ and $R_2$ are identical or different and represent each hydrogen, methyl, ethyl, isopropyl or n-butyl, and $R_1$ may be a phenyl or benzyl radical.

The radical $R_3$ may be especially a hydrogen atom, a methyl, ethyl, propenyl, propinyl, cyclopropylmethyl group, a methoxymethylene or ethoxymethylene group.

$R_4$ is preferably hydrogen, a methyl, ethyl, isopropyl or n-butyl group, or a hydroxy or alkoxy group having from 1 to 4 carbon atoms, or a carbalkoxy group having from 2 to 4 carbon atoms.

$R_5$ is especially an o-chlorophenyl, m-chlorophenyl, p-chlorophenyl, 2,4-dichlorophenyl group or one of the corresponding fluorine derivatives.

Especially favorable properties are found in those compounds of the formula I in which $R_1$ is methyl, ethyl or phenyl, $R_2$ is a methyl radical, $R_3$ is hydrogen, methyl, ethyl, cyclopropylmethyl or propinyl, $R_4$ is hydrogen and $R_5$ a phenyl or o- or m-chlorophenyl radical.

Examples of compounds of the invention are the following
1-methyl-8-phenyl-5,6,7,8-tetrahydropyrazolo(3,4-b) (1,4)diazepine-1H,4H-5,7-dione, 1,4-dimethyl-8-phenyl-5,6,7,8-tetrahydropyrazolo(3,4-b) (1,4)diazepine-1H,4H-5,7-dione, 4-ethyl-1-methyl-8-phenyl-5,6,7,8-tetrahydropyrazolo(3,4-b) (1,4) diazepine-1H,4H-5,7-dione, 4-allyl-1-methyl-8-phenyl-5,6,7,8-tetrahydropyrazolo(3,4-b) (1,4)diazepine-1H,4H-5,7-dione, 1-methyl-4-(2-propinyl)-8-phenyl-5,6,7,8-tetrahydropyrazolo-(3,4-b) (1,4)diazepine-1H,4H-5,7-dione, 4-cyclopropylmethyl-1-methyl-8-phenyl-5,6,7,8-tetrahydropyrazolo(3,4-b) (1,4)diazepine-1H,4H-5,7-dione, 1-methyl-4-(2-dimethylaminoethyl)-8-phenyl-5,6,7,8tetrahydropyrazolo-(3,4-b) (1,4)diazepine-1H,4H-5,7-dione, 4-(2-diethylaminoethyl)-1-methyl-8-phenyl-5,6,7,8-tetrahydropyrazolo(3,4-b) (1,4)diazepine-1H,4H-5,7-dione, 4-(2,2,2-trifluoroethyl)-1-methyl-8-phenyl-5,6,7,8-tetrahydropyrazolo(3,4-b) (1,4)diazepine-1H,4H-5,7-dione, 1methyl-4-(2-methylsulfonylethyl)-8-phenyl-5,6,7,8-tetrahydropyrazolo(3,4-b) (1,4)diazepine-1H,4H-5,7-dione, 1,3-dimethyl-4-ethyl-8-phenyl-5,6,7,8-tetrahydropyrazolo(3,4-b) (1,4)diazepine-1H,4H-5,7-dione, 4-allyl-1,3-dimethyl-8-phenyl-5,6,7,8-tetrahydropyrazolo-(3,4-b) (1,4)diazepine-1H,4H-5,7-dione, 1,3-dimethyl-4-(2-propinyl)-8-phenyl-5,6,7,8-tetrahydropyrazolo(3,4-b) (1,4)-diazepine-1H,4H-5,7-dione, 1,3-dimethyl-4-(dimethylaminoethyl)-8-phenyl-5,6,7,8-tetrahydropyrazolo(3,4-b) (1,4)diazepine-1H,4H-5,7-dione, 4-(2-diethylaminoethyl)-1,3-dimethyl-8-phenyl-5,6,7,8-tetrahydropyrazolo(3,4-b) (1,4)diazepine-1H,4H-5,7-dione, 1,3-dimethyl-4-(2,2,2-trifluoroethyl)-8-phenyl-5,6,7,8-tetrahydropyrazolo(3,4-b) (1,4)diazepine-1H,4H-5,7-dione, 2,3-dimethyl-4-(2-methylsulfonylethyl)-8-phenyl-5,6,7,8-tetrahydropyrazolo(3,4-b) (1,4)diazepine-1H,4H-5,7-dione, 1,4-diethyl-3-methyl-8-phenyl-5,6,7,8-tetrahydropyrazolo(3,4-b) (1,4)diazepine-1H,4H-5,7-dione, 4-allyl-1-ethyl-3-methyl-8-phenyl-5,6,7,8-tetrahydropyrazolo(3,4-b) (1,4)diazepine-1H,4H-5,7-dione, 1-ethyl-3-methyl-4-(2-propinyl)-8-phenyl-5,6,7,8-tetrahydropyrazolo(3,4-b) (1,4)diazepine-1H,4H5,7-dione, 4-cyclopropylmethyl-1-ethyl-3-methyl-8-phenyl-5,6,7,8-tetrahydropyrazolo(3,4-b) (1,4)diazepine-1H,4H-5,7-dione, 1-ethyl-3-methyl-4-(2-dimethylaminoethyl)-8-phenyl-5,6,7,8-tetrahydropyrazolo-(3,4-b) (1,4)diazepine-1H,4H-5,7-dione, 1-ethyl-4-(2-diethylaminoethyl)-3-methyl-8-phenyl-5,6,7,8-tetrahydropyrazolo-(3,4-b) (1,4)diazepine-1H,4H-5,7dione, 1-ethyl-4-(2,2,2-trifluoroethyl)-3-methyl-8-phenyl-5,6,7,8-tetrahydropyrazolo(3,4-b) (1,4)diazepine-1H,4H-5,7-dione, 1-ethyl-3-methyl-4-(2methylsulfonylethyl)-8-phenyl-5,6,7,8-tetrahydropyrazolo-(3,4-b) (1,4)diazepine-1H,4H-5,7-dione, 3-methyl-4-ethyl-1,8-diphenyl-5,6,7,8-tetrahydropyrazolo(3,4-b) (1,4)diazepine-1H,4H-5,7-dione, 4-allyl-3-methyl-1,8-diphenyl-5,6,7,8-tetrahydropyrazolo(3,4-b) (1,4)diazepine-1H,4H-5,7-dione, 3-methyl-1,8-diphenyl-4-(2-propinyl)-5,6,7,8-tetrahydropyrazolo(3,4-b) (1,4)diazepine-1H,4H-5,7-dione, 4-cyclopropylmethyl-3-methyl-1,8-diphenyl-5,6,7,8-tetrahydropyrazolo(3,4-b) (1,4)diazepine-1H,4H-5,7-dione, 3-methyl-4-(2-dimethylaminoethyl)-1,8-diphenyl-5,6,7,8-tetrahydropyrazolodiazepine-1H,4H,5,7-dione, 4-(2-diethylaminoethyl)-3-methyl-1,8-diphenyl-5,6,7,8-tetrahydropyrazolo(3,4-b) (1,4)diazepine-1H,4H-5,7-dione, 4-(2,2,2-trifluoroethyl)-3-methyl-1,8-diphenyl-5,6,7,8-tetrahydropyrazolo(3,4-b) (1,4)diazepine-1H,4H-5,7-dione, 3-methyl-4-(2-methylsulfonylethyl)-1,8-diphenyl-5,6,7,8-tetrahydropyrazolo(3,4-b) (1,4)diazepine-1H,4H-5,7-dione, 1-benzyl-4-ethyl-3-methyl-8-phenyl-5,6,7,8-tetrahydropyrazolo(3,4-b) (1,4)diazepine-1H,4H-5,7-dione, 1-benzyl-3-methyl-8-phenyl-4-(2-propinyl)-5,6,7,8-tetrahydropyrazolo(3,4-b) (1,4)diazepine-1H,4H-5,7-dione, 4-allyl-1-benzyl-3-methyl-8-phenyl-5,6,7,8-tetrahydropyrazolo(3,4-b) (1,4)diazepine-1H,4H-5,7-dione, 1-benzyl-4-cyclopropylmethyl-3-methyl-8-phenyl-5,6,7,8-tetrahydropyrazolo(3,4-b) (1,4)diazepine-1H,4H-5,7-dione, 1-benzyl-3-methyl-4-(2-dimethylaminoethyl)-8-phenyl-5,6,7,8-tetrahydropyrazolo(3,4-b) (1,4)diazepine-1H,4H-5,7-dione, 1-benzyl-4-(2-diethylaminoethyl)-3-methyl-8-phenyl-5,6,7,8-tetrahydropyrazolo(3,4-b) (1,4)diazepine-1H,4H-5,7-dione, 1-benzyl-4-(2,2,2-trifluoroethyl)-3-methyl-8-phenyltetrahydropyrazolo(3,4-b) (1,4)diazepine-1H,4H-5,7-dione, 1-benzyl-3-methyl-4-(2-methylsulfonylethyl)-8-phenyl-5,6,7,8-tetrahydropyrazolo(3,4-b) (1,4)diazepine-1H,4H-5,7-dione, 1,3,4,6-tetramethyl-8-phenyl-5,6,7,8-tetrahydropyrazolo-(3,4-b) (1,4)diazepine-1H,4H-5,7-dione, 1,3,6-trimethyl-8-phenyl-5,6,7,8-tetrahydropyrazolo(3,4-b) (1,4)-diazepine-1H,4H-5,7-dione, 1,3-dimethyl-6-hydroxy-8-phenyl-5,6,7,8-tetrahydropyrazolo(3,4-b) (1,4)diazepine-1H,4H-5,7-dione, 1,3-dimethyl-6-oxydimethylcarbamoyl-8-phenyl-5,6,7,8-tetrahydropyrazolo(3,4-b) (1,4)diazepine-1H,4H-5,7-dione, 6-hydroxy-1,3,4-trimethyl-8-phenyl-5,6,7,8-tetrahydropyrazolo(3,4-b) (1,4)diazepine-1H,4H-5,7-dione, 1,3,4-trimethyl-6-oxydimethylcarbamoyl-8-phenyl-5,6,7,8-tetrahydropyrazolo-(3,4-b) (1,4)diazepine-1H,4H-5,7-dione, 6-hydroxy-1-ethyl-3-methyl-8-phenyl-5,6,7,8-tetrahydropyrazolo(3,4-b) (1,4)-diazepine-1H,4H-5,7-dione, 1-ethyl-6-hydroxy-3,4-dimethyl-8-phenyl-5,6,7,8-tetrahydropyrazolo(3,4-b) (1,4)diazepine-1H,4H-5,7-dione, 1-ethyl-3-methyl-6-oxydimethylcarbamoyl-8-phenyl-5,6,7,8-tetrahydropyrazolo(3,4-b) (1,4)diazepine-1H,4H-5,7-dione, 1-ethyl-3,4-dimethyl-6-oxydimethylcarbamoyl-8-phenyl-5,6,7,8-tetrahydropyrazolo(3,4-b) (1,4)diazepine-1H,4H-5,7-dione, 6-hydroxy-3-methyl-1,8-diphenyl-5,6,7,8-tetrahydropyrazolo(3,4-b) (1,4)diazepine-1H,4H-5,7-dione, 6-hydroxy-3,4-dimethyl-1,8-diphenyl-5,6,7,8-tetrahydropyrazole(3,4-b) (1,4)diazepine-1H,4H-5,7-dione, 3-methyl-6-oxydimethylcarbamoyl-1,8-diphenyl-5,6,7,8-tetrahydropyrazolo(3,4-b) (1,4)diazepine-1H,4H-5,7-dione, 3,4-dimethyl-6-oxydimethylcarbamoyl-1,8-diphenyl-5,6,7,8-tetrahydropyrazolo(3,4-b) (1,4)diazepine-1H,4H-5,7-dione, 1-benzyl-3,6-dimethyl-8-phenyl-5,6,7,8-tetrahydropyrazolo(3,4-b) (1,4)-diazepine-1H,4H-5,7-dione, 1-benzyl-3,4,6-trimethyl-8-phenyl-5,6,7,8-tetrahydropyrazolo(3,4-b) (1,4)diazepine-1H,4H-5,7-dione, 1-benzyl-6-hydroxy-3-methyl-8-phenyl-5,6,7,8-tetrahydropyrazolo(3,4-b) (1,4)diazepine-1H,4H-dione, 1-benzyl-6-hydroxy-3,4-dimethyl-8-phenyl-5,6,7,8-tetrahydropyrazolo(3,4-b) (1,4)diazepine-1H,4H-5,7-dione, 1-benzyl-3-methyl-6-oxydimethyl-carbamoyl-8-phenyl-5,6,7,8-tetrahydropyrazolo(3,4-b) (1,4)diazepine-1H,4H-5,7-dione, 1-benzyl-3,4-dimethyl-6-oxydimethylcarbamoyl-8-phenyl-5,6,7,8-tetrahydropyrazolo(3,4-b) (1,4)diazepine-1H,4H-5,7-dione, 1-methyl-8-(2-chlorophenyl)-5,6,7,8-tetrahydropyrazolo-(3,4-b) (1,4)diazepine-1H,4H-5,7-dione, 1,4-dimethyl-8-(2,4-dichlorophenyl)-5,6,7,8-tetrahydropyrazolo(3,4-b) (1,4)-diazepine-1H,4H-5,7-dione, 1-methyl-4-allyl-8-(2-pyridyl)-5,6,7,8-tetrahydropyrazolo(3,4-b) (1,4)diazepine-1H,4H-5,7-dione, 1-methyl-4-(2-propinyl)-8-(2-trifluoromethylphenyl)-5,6,7,8-tetrahydropyrazolo(3,4-b) (1,4)diazepine-1H,4H-5,7-dione, 1-methyl-4-cyclopropylmethyl-8-(o-tolyl)-5,6,7,8-tetrahydropyrazolo(3,4-b) (1,4)diazepine-1H,4H-5,7-dione, 1-methyl-4-(2-dimethylaminoethyl)-8-(3-chlorophenyl)-5,6,7,8-tetrahydropyrazolo(3,4-b) (1,4)diazepine-1H,4H-5,7-dione, 1-methyl-4-(2-diethylaminoethyl)-8-(3,4-dichlorophenyl)-5,6,7,8-tetrahydropyrazolo(3,4-b) (1,4)diazepine-1H,4H-5,7-dione, 1-methyl-4-(2,2,2-trifluoroethyl)-8-(4-chlorophenyl)-5,6,7,8-tetrahydropyrazolo(3,4-b) (1,4)diazepine-1H,4H-5,7-dione, 1-methyl-4-(2-methylsulfonylethyl)-8-(p-tolyl)-5,6,7,8-tetrahydropyrazolo(3,4-b) (1,4)diazepine-1H,4H-5,7-dione, 1,3-dimethyl-8-(o-tolyl)-5,6,7,8-tetrahydropyrazolo-(3,4-b) (1,4)diazepine-1H,4H-5,7-dion, 1,3,4-trimethyl-8-(3-chlorophenyl)-5,6,7,8-tetrahydropyrazolo(3,4-b) (1,4)-diazepine-1H,4H-5,7-dione, 4-allyl-1,3-dimethyl-8-(3,4-dichlorophenyl)-5,6,7,8-tetrahydropyrazolo(3,4-b) (1,4)-diazepine-1H,4H-5,7-dione, 1,3-dimethyl-4-(2-propinyl)-8-(4-chlorophenyl)-5,6,7,8-tetrahydropyrazolo(3,4-b) (1,4)-diazepine-1H,4H-5,7-dione, 1,3-dimethyl-4-cyclopropylmethyl-8-(p-tolyl)-5,6,7,8-tetrahydropyrazolo(3,4-b) (1,4)-diazepine-1H,4H-5,7-dione, 1,3-dimethyl-4-(2-dimethylaminoethyl)-8-(2-chlorophenyl)-5,6,7,8-tetrahydropyrazolo-(3,4-b) (1,4)diazepine-1H,4H-5,7-dione, 1,3-dimethyl-4-(2-diethylaminoethyl)-8-(2,4-dichlorophenyl)-5,6,7,8-tetrahydropyrazolo(3,4-b) (1,4)diazepine-1H,4H-5,7-dione, 1,3-dimethyl-4-(2,2,2-trifluoroethyl)-8-(2-cyanophenyl)-5,6,7,8-tetrahydropyrazolo(3,4-b) (1,4)diazepine-1H,4H-5,7-dione, 1,3-dimethyl-4-(2-methylsulfonylethyl)-8-(2-trifluoromethylphenyl)-5,6,7,8-tetrahydropyrazolo(3,4-b) (1,4)diazepine-1H,4H-5,7-dione, 1-ethyl-3,4-dimethyl-8-(2-chlorophenyl)-5,6,7,8-tetrahydropyrazolo(3,4-b) (1,4)diazepine-1H,4H-5,7-dione, 4-allyl-1-ethyl-3-methyl-8-(2,4-dichlorophenyl)-5,6,7,8-tetrahydropyrazolo(3,4-b) (1,4)diazepine-1H,4H-5,7-dione, 1-ethyl-3-methyl-4-(2-propinyl)-8-(2-pyridyl)-5,6,7,8-tetrahydropyrazolo(3,4-b) (1,4)diazepine-1H,4H-5,7-dione, 4-cyclopropylmethyl-1-ethyl-3-methyl-8-(2-trifluoromethylphenyl)-5,6,7,8-tetrahydropyrazolo(3,4-b) (1,4)diazepine-1H,4H-5,7-dione, 1-ethyl-3-methyl-4-(2-dimethylaminoethyl)-8-o-tolyl)-5,6,7,8-tetrahydropyrazolo(3,4-b) (1,4)diazepine-1H,4H-5,7-dione, 1-ethyl-3-methyl-4-(2-methylsulfonylethyl)-8-(4-chlorophenyl)-5,6,7,8-tetrahydropyrazolo(3,4-b) (1,4)diazepine-1H,4H-5,7-dione, 1-phenyl-3,4-dimethyl-8-(m-tolyl)-5,6,7,8-tetrahydropyrazolo(3,4-b) (1,4)diazepine-1H,4H-5,7-dione, 4-allyl-3-methyl-1-phenyl-8-(3,4-dichlorophenyl)-5,6,7,8-tetrahydropyrazolo(3,4-b) (1,4)diazepine-1H,4H-5,7-dione, 3-methyl-1-phenyl-4-(2-propinyl)-8-(3-chlorophenyl)-5,6,7,8-tetrahydropyrazolo(3,4-b) (1,4)diazepine-1H,4H-5,7-dione, 4-cyclopropylmethyl-3-methyl-1-phenyl-8-(2-cyanophenyl)-5,6,7,8-tetrahydropyrazolo(3,4-b) (1,4)diazepine-1H,4H-5,7-dione, 3-methyl-4-(2-dimethylaminoethyl)-1-phenyl-8-(2-pyridyl)-5,6,7,8-tetrahydropyrazolo(3,4-b) (1,4)diazepine-1H,4H-5,7-dione, 4-(2-diethylaminoethyl)-3-methyl-1-phenyl-8-(2-chlorphenyl)-5,6,7,8-tetrahydropyrazolo(3,4-b) (1,4)diazepine-1H,4H-5,7-dione, 4-(2,2,2-trifluoroethyl)-3-methyl-1-phenyl-8-(o-tolyl)-5,6,7,8-tetrahydropyrazolo(3,4-b) (1,4)diazepine-1H,4H-5,7-dione, 3-methyl-1-phenyl-4-(2-methylsulfonylethyl)-8-(2,4-dichlorophenyl)-5,6,7,8-tetrahydropyrazolo(3,4-b) (1,4)diazepine-1H,4H-5,7-dione, 1-benzyl-3,4-dimethyl-8-(2-chlorophenyl)-5,6,7,8-tetrahydropyrazolo(3,4-b) (1,4)diazepine-1H,4H-5,7-dione, 4-allyl-1-benzyl-3-methyl-8-(3,4-dichlorophenyl)-5,6,7,8-tetrahydropyrazole(3,4-b) (1,4)diazepine-1H,4H-5,7-dione, 1-benzyl-3-methyl-4-(2-propinyl)-8-(o-tolyl)-5,6,7,8-tetrahydropyrazolo(3,4-b) (1,4)diazepine-1H,4H-5,7-dione, 1-benzyl-4-cyclopropylmethyl-3-methyl-8-(4-chlorophenyl)-5,6,7,8-tetrahydropyrazolo(3,4-b) (1,4)diazepine-1H,4H-5,7-dione, 1-benzyl-3-methyl-4-(2-dimethylaminoethyl)-8-(3-chlorophenyl)-5,6,7,8-tetrahydropyrazolo(3,4-b) (1,4)diazepine-1H,4H-5,7-dione, 1-benzyl-3-methyl-4-(2-diethylaminoethyl)-8-(2-trifluoromethylphenyl)-5,6,7,8-tetrahydropyrazolo(3,4-b) (1,4)diazepine-1H,4H-5,7-dione, 1-benzyl-3-methyl-4-(2,2,2-trifluoroethyl)-8-(4-chlorophenyl)-5,6,7,8-tetrahydropyrazolo(3,4-b) (1,4)diazepine-1H,4H,5,7-dione, 1benzyl-3-methyl-4-(2-methylsulfonylethyl)-8-(2-cyanophenyl)-5,6,7,8-tetrahydropyrazolo(3,4-b) (1,4)diazepine-1H,4H-5,7-dione, 1,3,6-trimethyl-8-(2-trifluoromethylphenyl)-5,6,7,8-tetrahydropyrazolo(3,4-b) (1,4)diazepine-1H,4H-5,7-dione, 1,3,4,6-tetramethyl-8-(o-tolyl)-5,6,7,8-tetrahydropyrazolo(3,4-b) (1,4)diazepine-1H,4H-5,7-dione, 1,3-dimethyl-6-hydroxy-8-(2,4-dichlorophenyl)-5,6,7,8-tetrahydropyrazolo(3,4-b) (1,4)diazepine-1H,4H-5,7-dione, 1,3,4-trimethyl-6-hydroxy-8-(2-pyridyl)-5,6,7,8-tetrahydropyrazolo(3,4-b) (1,4)diazepine-1H,4H-5,7-dione, 1,3-dimethyl-6-oxydimethylcarbamoyl-8-(2-chlorophenyl)-5,6,7,8-tetrahydropyrazolo(3,4-b) (1,4)-diazepine-1H,4H-5,7-dione, 1,3,4-trimethyl-6-oxydimethylcarbamoyl-8-(m-tolyl)-5,6,7,8-tetrahydropyrazolo(3,4-b) (1,4)diazepine-1H,4H-5,7-dione, 1-ethyl-3-methyl-6-hydroxy-8-(2,4-dichlorophenyl)-5,6,7,8-tetrahydropyrazolo(3,4-b) (1,4)diazepine-1H,4H-5,7-dione, 1-ethyl-3,4-dimethyl-6-hydroxy-8-(2-cyanophenyl)-5,6,7,8-tetrahydropyrazolo(3,4-b) (1,4)diazepine-1H,4H-5,7-dione, 1-ethyl-3-methyl-6-oxydimethylcarbamoyl-8-(2-pyridyl)-5,6,7,8-tetrahydropyrazolo(3,4-b) (1,4)diazepine-1H,4H-5,7-dione, 1-ethyl-3,4-dimethyl-6-oxydimethylcarbamoyl-8-(3-chlorophenyl)-5,6,7,8-tetrahydropyrazolo(3,4-b) (1,4)diazepine-1H,4H-5,7-dione, 1-ethyl-3,6-dimethyl-8-(4-chlorophenyl)-5,6,7,8-tetrahydropyrazolo-(3,4-b) (1,4)diazepine-1H,4H-5,7-dione, 1-ethyl-3,4,6-trimethyl-8-(m-tolyl)-5,6,7,8-tetrahydropyrazolo(3,4-b) (1,4)-diazepine-1H,4H-5,7-dione, 3,6-dimethyl-1-phenyl-8-(3,4-dichlorophenyl)-5,6,7,8-tetrahydropyrazolo(3,4-b) (1,4)diazepine-1H,4H-5,7-dione, 3,4,6-trimethyl-1-phenyl-8-(2-trifluoromethylphenyl)-5,6,7,8-tetrahydropyrazolo(3,4-b) (1,4)diazepine-1H,4H-5,7-dione, 3-methyl-1-phenyl-6-hydroxy-8-(2-cyanophenyl)-5,6,7,8-tetrahydropyrazolo(3,4-b) (1,4)-diazepine-1H,4H-5,7-dione, 3,4-dimethyl-1-phenyl-6-oxydimethylcarbamoyl-8-(2-bromophenyl)5,6,7,8-tetrahydropyrazolo-(3,4-b) (1,4-diazepine-1H,4H-5,7-dione, 3,4-dimethyl-1-phenyl-6-hydroxy-8-(3-bromophenyl)-5,6,7,8-tetrahydropyrazolo-(3,4-b) (1,4)diazepine-1H,4H-5,7-dione, 3-methyl-1-phenyl-6-oxydimethylcarbamoyl-8-(4-bromophenyl)-5,6,7,8-tetrahydropyrazolo(3,4-b) (1,4)diazepine-1H,4H-5,7-dione, 1-benzyl-3,6-dimethyl-8-(2-pyridyl)-5,6,7,8-tetrahydropyrazolo(3,4-b) (1,4)diazepine-1H,4H-5,7-dione, 1-benzyl-3,4,6-trimethyl-8-(o-tolyl)-5,6,7,8-tetrahydropyrazolo(3,4-b) (1,4)diazepine-1H,4H-5,7-dione, 1-benzyl-6-hydroxy-3-methyl-8-(2-trifluoromethyl)-5,6,7,8-tetrahydropyrazolo(3,4-b) (1,4)diazepine-1H,4H-5,7-dione, 1-benzyl-6-hydroxy-3,4-dimethyl-8-(2,4-dichlorophenyl)-5,6,7,8-tetrahydropyrazolo(3,4-b) (1,4)diazepine-1H,4H-5,7-dione, 1-benzyl-3-methyl-6-oxydimethylcarbamoyl-8-(2-cyanophenyl)-5,6,7,8-tetrahydropyrazolo(3,4-b) (1,5)-diazepine-1H,4H-5,7-dione, 1-benzyl-3,4-dimethyl-6-oxydimethylcarbamoyl-8-(3,4-dichlorophenyl)-5,6,7,8-tetrahydropyrazolo(3,4-b) (1,4)diazepine-1H,4H-5,7-dione.

Subject of the invention are furthermore processes for the preparation of these compounds and pharmaceutical formulations thereof and their use as medicaments.

The preparation may be carried out in known manner by (a) cyclizing a compound of the formula

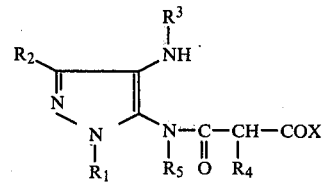

in which $R_1$ through $R_5$ are as defined above and X is a hydroxy group, a mercapto group, a halogen atom, an alkoxy group, an alkylmercapto group, an amino group, an alkylamino group, a dialkylamino group, a benzoyloxy group, an aryloxy group, an acyloxy group or the group $N_3$, to form a seven-membered ring; or (b) condensing a compound of the formula

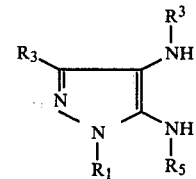

in which $R_1$ through $R_3$ and $R_5$ are as defined above, with an activated malonic acid derivative, for example malonic acid dihalide, malonic ester, carbon suboxide, medrum'acid or with malonic acid per se to form a seven-membered ring; or (c) cyclizing a compound of the formula

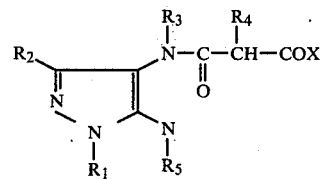

in which $R_1$ through $R_5$ are as defined above and X represents the groups indicated sub (a), according to the method of (a) to form a seven-membered ring, and optionally substituting in known manner the radicals, $R_3$ and $R_4$ of those compounds obtained where one of them or both are hydrogen by alkylation or acylation, either simultaneously or one after the other.

The process (a) can be carried out with or without solvent by heating to 50°–250° C. optionally with addition of a condensation agent such as usually employed for these reactions. Suitable solvents are for example: aliphatic alcohols (methanol, ethanol), dioxan, dimethyl formamide, benzene, toluene, aqueous or alcoholic hydrochloric acid, glacial acetic acid, polyphosphoric acid, $H_2SO_4$; the latter three being condensation agents which can be used in the cited solvents. Further condensation agents are for example metal alcoholates, especially alkali metal alcoholates, alkali metal amides, alkali metal hydrides (NaH), strong acids such as trifluoroacetic acid, p-toluenesulfonic acid, or also dehydration agents such as dicyclohexyl-carbo-diimide, etc. Halogen atoms suitable for the process (a) are preferably Cl, Br or the halogen-like $N_3$ group. In the case where X is an alkoxy, alkylmercapto, alkylamino or dialkylamino group, these groups contain generally alkyl radicals having from 1 to 6 carbon atoms. When X is an acyloxy group, it is preferably an aliphatic acyl group having from 2 to 6 carbon atoms. The preferred aryloxy group is a phenoxy group.

The process (b) comprises reacting the activated malonic acid derivative with the use of a suitable inert solvent such as benzene, toluene, xylene, ether, tetrahydrofuran, dioxan or dimethyl formamide, at room temperature or preferably at boiling temperature of the corresponding solvent. In certain cases it is advantageous to add a tertiary organic base such as pyridine or triethylamine in order to ensure that the reaction proceeds as intended. The reaction with malonic acid is advantageously carried out with the use of strong acids such as HCl, $H_2SO_4$, trifluoroacetic acid, polyphosphoric acid etc.

The process (c) is characterized by the fact that cyclization to form the seven-membered ring is carried out under the same conditions as described for process (a).

Alternatively, the radicals $R_3$ and $R_4$ can be introduced later by alkylation or acylation according to known methods. For example, compounds of the formula I, in which $R_3$ and $R_4$ are hydrogen may be converted to a monoalkali metal salt with proton acceptors such as sodium hydride, sodium amide, potassium-tert.-butylate or finely dispersed sodium in an inert solvent, and this salt can be alkylated or acylated in known manner. Suitable alkylation agents are for example alkyl halides of the formula RHal, or esters of the formulae $ArSO_2OR$ or $SO_2(OR)_2$; Hal being a halogen atom (especially Cl, Br, I) and Ar an aromatic radical such as phenyl or phenyl substituted by one or more lower alkyl radicals. R stands for the corresponding groups cited sub $R_3$ (except H). Acylation can be carried out under the same conditions. Suitable acylation agents are ketenes, or acid halides, acid anhydrides, acid esters or aliphatic carboxylic acids having from 2 to 6 carbon atoms or carbonic acid semiester halides having from 1 to 6 carbon atoms.

The starting materials used for the processes (a), (b) and (c) are obtained for example in the following manner: (a) A compound of the formula

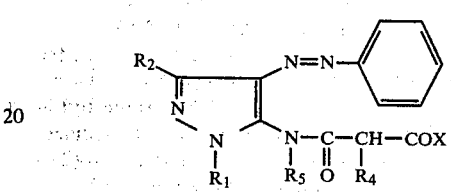

V in which $R_1$, $R_2$ and $R_5$ are as defined above, is reacted with a compound of the formula

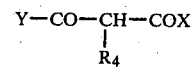

VI in which $R_4$ and X are as defined above and Y is a chlorine or bromine atom, an azido group ($N_3$), or an alkyloxy or aryloxy group, in an inert solvent such as dioxan, tetrahydrofuran, chloroform, benzene or toluene, at temperatures of from 0° to 200° C., with or without addition of an acid acceptor, to form a compound of the formula

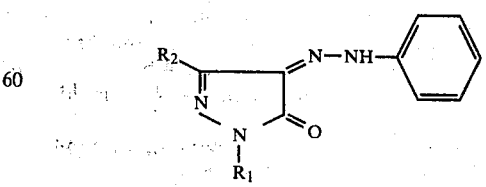

VII

In this compound, the azo group is split by reduction, so that the amino compound of formula II is formed in which $R_3$ is hydrogen. The radical $R_3$ may be introduced for example by alkylation or acylation according to known methods. The azo group can be split by catalytic hydrogenation (with Pd, Pt, Raney nickel in alcohols, dioxan, tetrahydrofuran at 0°-60° C. and under a $H_2$ pressure of from 1 to 50 atmospheres), or by chemical reduction, for example with sodium dithionite in aqueous or alcoholic solution, with $SnCl_2$ in HCl, or with zinc in glacial acetic acid or a neutral, acidic or alkaline-aqueous solution.

The starting materials of the formula V are obtained according to the method described by F. A. Amer, A. H. Harhash and M. L. Awad, Z. Naturforsch. 33b, 660–662 (1978), or can be synthetized as follows:

A pyrazolone of the formula

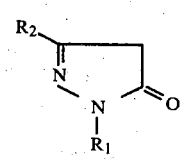

is reacted at 0°–5° C. with benzene-diazonium chloride in glacial acetic acid to form the phenylhydrazone of the formula

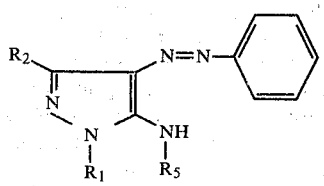

which can be chlorinated in 5-position in boiling $POCl_3$ to give the 4-benzene-azo-5-chloropyrazole of the formula

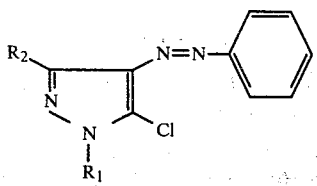

Subsequently, the chlorine is replaced by a correspondingly substituted aniline or pyridine at 100°–160° C. with or without solvent, thus obtaining the compound of formula V.

Compounds of the formula II can alternatively be obtained according to the following method:

A compound of the formula X

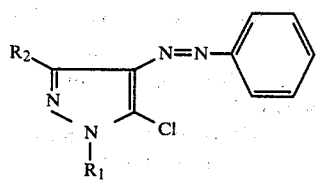

(synthesis see above) is converted to a compound of the formula VII with a compound of the formula

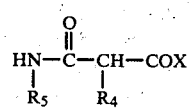    XI in which $R_4$ and $R_5$ are as defined above and X stands for the cited radicals with the exception of halogen, $NH_2$, alkylamino and azido ($N_3$). The operations are generally carried out in an inert solvent such as dioxan, tetrahydrofuran, dimethylformamide, with addition of a proton acceptor such as NaH, sodium amide, or finely distributed sodium. The reaction temperatures are from 0° to 150° C.

Compounds of the formula II in which X is halogen can be obtained for example from compounds of the formula II in which X is OH by reaction with halogenation agents such as thionyl chloride or phosphorus pentachloride at temperatures of from 0° to 100° C. in inert solvents such as benzene, toluene, dioxan or tetrahydrofuran. The carboxylic acids of the formula II (X=OH) can be obtained for example from the corresponding esters (X=alkyloxy, aryloxy or benzyloxy) by converting them to the corresponding acid under gentle conditions, for example by hydrogenation (in the case where X is benzyloxy), or by very gentle hydrolysis (in the case where X is aryloxy or a branched alkyloxy radical such as tert.-butoxy). Compounds of the formula II in which X is an acyloxy group can be prepared from the corresponding halides by reaction with the corresponding metal salts of carboxylic acids, for example with sodium acetate or silver benzoate, in inert solvents such as acetone, dioxan, ether at temperatures of from −20° to 100° C.

Compounds of the formula II in which X is an azido group can be prepared for example from the corresponding halides by reaction with alkali metal azides in inert solvents such as acetone, dioxan or dimethyl sulfoxide, at temperatures of from 0° to 100° C., or from esters (X=O-alkyl or O-aryl) by reaction with hydrazine, optionally in an inert solvent such as ethanol, dioxan, or tetrahydrofuran, at temperatures of from 0° to 100° C., and subsequent reaction of the hydrazide with nitrous acid or nitrous gases in inert solvents such as alcohols, dioxan, or dimethyl formamide, at temperatures of from 0° to 50° C.

The starting products of the formula XI can be prepared as follows:

An amine $R_5$-$NH_2$ where $R_5$ is as defined above is reacted with a compound of the formula VI, in which $R_4$ and X are as defined above (except halogen, $NH_2$, alkylamino and azido for X), and Y is a chlorine or bromine atom, an azido group or an alkyloxy or aryloxy group, in an inert solvent such as dioxan, tetrahydrofuran, chloroform, or an an excess of compound VI, at temperatures of from 0° to 200° C. Operations may be in analogy to Chem. Ber. 17, 739 et sequ. (1884) or J. Indian Chem. Soc. 37, 591–593 (1960).

(b) In the compound of the formula V, the azo group is split by reduction under the cited conditions to form a compound of the formula III in which $R_3$ is hydrogen. In the case where the radical $R_3$ is an alkyl group, it can be introduced according to the indications of Chem. Ber. 34, 4204 (1902) and 37, 552 (1904) by cyclization with formic acid to give pyrazolo-imidazole, alkylation by means of alkyl iodide at the imidazole nitrogen atom and subsequent splitting of the imidazole ring by means of alkali. In the case of acylation, the diamine III can be reacted under gentle conditions, for example with carboxylic acid halides, anhydrides or esters; the primary amino group being selectively separated in this reaction, which is preferably carried out in an inert solvent such as ether, dioxan, tetrahydrofuran or chloroform, with or without addition of a proton acceptor, at a temperature of from 0° to 100° C.

(c) Compounds of the formula IV can be obtained by reaction of compounds of the formula III with compounds of the formula VI; the amino group in 4-position of the pyrazole ring being selectively separated in this reaction, which is carried out in an inert solvent such as benzene, toluene, dioxan, tetrahydrofuran or chloroform, with or without addition of an acid acceptor, at a temperature of from 0° to 150° C.

The compounds of the invention are suitable for the manufacture of medicaments, which may contain one or more of the compounds of the invention or mixtures thereof with other pharmaceutically active substances. For the manufacture of such medicaments, the usual pharmaceutical carriers and auxiliaries, and known galenic processes may be employed. The medicaments may be administered enterally, parenterally, orally or perlingually, for example in the form of tablets, capsules, pills, dragees, suppositories, jellies, creams, powders, liquids, dusting powders or aerosols. Suitable liquids are for example oily or aqueous solutions or suspensions, emulsions, injectable aqueous solutions or suspensions.

The compounds of the invention have excellent anxiolytic properties, and they can therefore be administered in cases of insomnia, emotional tension and vegetative disturbances.

The pharmaceutical formulations contain generally from 1 to 10% of the active component(s) of the invention.

The anxiolytic action is combined with a very low sedation and a good tolerability ($LD_{50} \gg 1200$ mg/kg p.o. in mice). This results from tests by which the influence of the compounds of the invention on the motor activity, the hexobarbital anaesthesia and the cardiazol spasm of mice was measured. Furthermore, the taming-of-the-golden-hamster test and the Geller anxiolysis test in rats was carried out and evaluated.

The lowest active dose is 5 mg/kg orally, 2.5 mg/kg sublingually, 1 mg/kg intravenously. Generally, an adult is administered per day from 5 to 50 mg/kg orally, from 2.5 to 25 mg/kg sublingually or from 1 to 10 mg/kg intravenously.

Accordingly, it is recommended to administer to an adult 3 times a day from 1 to 3 tablets containing from 10 to 100 mg of active substance, or in the case of intravenous injection 1 to 3 times a day an ampoule of from 2 to 4 ml containing from 0.5 to 5 mg of active substance.

The following examples illustrate the invention.

EXAMPLE 1

1-ethyl-3-methyl-8-phenyl-5,6,7,8-tetrahydropyrazolo(3,4-b)-(1,4)diazepine-1H,4H-5,7-dione (a) 4-amino-5-anilino-1-ethyl-3-methylpyrazole. 30.5 g (0.1 mol) 5-anilino-4-benzene-azo-1-ethyl-3-methyl pyrazole are hydrogenated at room temperature and under normal pressure in 250 ml ethanol with 60 g Raney nickel. After the absorption of hydrogen is complete, the batch is suction-filtered from the catalyst and the reaction solution is evaporated in vacuo. Petroleum ether is added to the residue, and the precipitate is suction-filtered. Recrystallization from chloroform yields the analytically pure product.

(b) 5-anilino-4-α-carbethoxyacetylamino-1-ethyl-3-methyl-pyrazole. 2.2 g 4-amino-5-anilino-1-ethyl-3-methylpyrazole (0.01 mol) are dissolved in 20 ml toluene, 1 ml malonic acid monoethyl ester chloride (0.012 mol) is slowly added dropwise at room temperature, and agitation is continued for one hour at this temperature. The toluene is removed in vacuo, the residue is absorbed in chloroform shaked in icecold NaHCO3 solution, washed with water and dried with Na2SO4. After evaporation of the solvent, a yellowish oil remains which does not crystallize.

(c) 1-ethyl-3-methyl-8-phenyl-5,6,7,8-tetrahydropyraolo(3,4-b) (1,4)diazepine-1H,4H-5,7-dione. 15 ml of a 1-molar sodium methanolate solution are added to 3.3 g 5-anilino-4-alpha-carbethoxy-acetylamino-1-ethyl-3-methylpyrazol (0.01 mol) dissolved in 100 ml ethanol, and the batch is agitated for 8 hours at room temperature. Subsequently, it is neutralized with HCl, evaporated in vacuo, the residue is agitated with ether, and suction-filtered. Recrystallization from isopropanol yields the analytically pure product. M.p.: 196°–197° C.

EXAMPLE 2

1-ethyl-3,4-dimethyl-8-phenyl-5,6,7,8-tetrahydropyrazolo-(3,4-b) (1,4)diazepine-1H,4H-5,7-dione.

2.84 g 1-ethyl-3-methyl-8-phenyl-5,6,7,8-tetrahydropyrazolo(3,4-b) (1,4)diazepine-1H,4H-5,7-dione (0.01 mol) are dissolved in 35 ml DMF, and 0.57 g of 80% NaH (0.01 mol) is added at room temperature under a nitrogen atmosphere. After agitation for 1 hour, the solvent is removed in vacuo, the residue is absorbed in chloroform, washed with water and dried with Na2SO4. The chloroform is evaporated and the product is recrystallized from isopropanol/water. M.p.: 125°–126° C.

EXAMPLE 3

1,3-dimethyl-8-phenyl-5,6,7,8-tetrahydropyrazolo(3,4-b) (1,4)diazepine-1H,4H-5,7-dione A solution of 500 mg of 4-amino-5-anilino-1,3-dimethylpyrazole (0.004 mol) is slowly added dropwise with ice cooling to a solution of 280 mg carbon suboxide (preparation see H. Staudinger, S. Bereza, Ber. 41, 4461 (1908)) (0.4 mol) in 70 ml ether. Subsequently, agitation is continued for a further hour at 0° C., and the precipitate is suction-filtered. Recrystallization from isopropanol gives the product. M.p.: 249° C.

EXAMPLE 4

3-methyl-1,8-diphenyl-5,6,7,8-tetrahydropyrazolo(3,4-b) (1,4)diazepine-1H,4H-5,7-dione (a) 4-benzene-azo-5-(N-α-methoxycarbonylacetylanilino)-3-methyl-1-phenylpyrazole.

(1) 2.4 g NaH (0.1 mol) are added at room temperature and under a nitrogen atmosphere to a solution of 19.3 g (0.1 mol) malonic acid methyl ester monoanilide in 100 ml DMF, and agitation is continued for a further 30 minutes. Subsequently, a solution of 30 g (0.1 mol) 4-benzene-azo-5-chloro-3-methyl-1-phenylpyrazole in 50 ml DMF is slowly added dropwise with cooling, and the batch in then heated for 1 hour at 50° C. 10 ml ethanol are added as well as 5 ml glacial acetic acid, and the solution is evaporated in vacuo. The residue is absorbed in chloroform, washed with water, dried with Na2SO4 and evaporated. Recrystallization from petroleum ether gives yellow crystals having a melting point of 158°–159° C.

(2) 3.5 g (0.01 mol) 5-anilino-4-benzene-azo-3-methyl-1-phenylpyrazole are reacted in 50 ml boiling benzene with 1.36 ml (0.012 mol) malonic acid monomethyl ester chloride, until the HCl development has stopped. The benzene is then removed in vacuo, the residue is absorbed in CHCl3, washed with cold NaHCO3 solution and water, dried and evaported. Recrystallization from petroleum ether gives yellow crystals being identical with the compound described under 4(a)(1).

(b) 4-Amino-5-(N-α-methoxycarbonylacetylanilino)-3-methyl-1-phenylpyrazole. 4.5 g (0.01 mol) 4-benzene-azo-5-(N-α-methoxycarbonylacetylanilino)-3-methyl-1-phenylpyrazole, dissolved in 100 ml ethanol, are hydrogenated at room temperature and under a hydrogen pressure of 1 atmosphere with 10 g Raney nickel. After the end of the hydrogen absorption, the batch is suction-filtered from the catalyst, and the reaction solution is evaporated in vacuo. A colorless oil which cannot be crystallized remains as residue.

(c) 3-methyl-1,8-diphenyl-5,6,7,8-tetrahydropyrazolo-(3,4-b) (1,4)diazepine-1H,4H-5,7-dione. 3.6 g (0.01 mol) of the oil obtained according to 4(b) are dissolved in 100 ml ethanol. After addition of 1 ml concentrated HCl, the solution is refluxed until the starting material has disappeared (TLC control). Subsequently, the solution is evaporated in vacuo, the residue absorbed in chloroform, washed with NaHCO3 solution and water, dried and evaporated. Recrystallization from isopropanol yields white crystals, m.p. 262° C.

According to the above methods, the following further compounds were prepared:

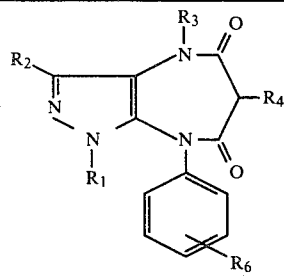

| Ex. | $R_1$ | $R_2$ | $R_3$ | $R_4$ | $R_6$ | b.p. (°C.) | prepared acc. to Ex. |
|---|---|---|---|---|---|---|---|
| 5 | —$C_2H_5$ | —$CH_3$ | H | H | 2-$CH_3$ | 221 | 4 |
| 6 | —$C_2H_5$ | —$CH_3$ | H | H | 2-Cl | 206–207 | 4 |
| 7 | —$CH_3$ | —$CH_3$ | H | H | 4-$CH_3$ | 251 | 4 |
| 8 | —$C_2H_5$ | —$CH_3$ | H | H | 4-Cl | 186 | 4 |
| 9 | —$C_2H_5$ | —$CH_3$ | H | H | 4-$CH_3$ | 183–184 | 4 |
| 10 | —$CH_3$ | —$CH_3$ | H | H | 4-Cl | 261–262 | 4 |
| 11 | —$CH_3$ | —$CH_3$ | H | H | 2-$CH_3$ | 235 | 4 |
| 12 | —$CH_3$ | —$CH_3$ | H | H | 2-Cl | 228 | 4 |
| 13 | —$C_6H_5$ | —$CH_3$ | H | H | 4-$CH_3$ | 245–246 | 4 |
| 14 | —$CH_3$ | —$CH_3$ | —$CH_3$ | H | 4-$CH_3$ | 165 | 2 |
| 15 | —$CH_3$ | —$CH_3$ | —$CH_3$ | H | 2-$CH_3$ | 163 | 2 |
| 16 | —$CH_3$ | —$CH_3$ | —$CH_3$ | H | 4-Cl | 165–166 | 2 |
| 17 | —$C_2H_5$ | —$CH_3$ | —$CH_3$ | H | 2-Cl | 181–182 | 2 |
| 18 | —$C_2H_5$ | —$CH_3$ | —$CH_3$ | H | 4-$CH_3$ | 157 | 2 |
| 19 | —$C_2H_5$ | —$CH_3$ | —$CH_3$ | —$CH_3$ | 4-$CH_3$ | 152 | 2 |
| 20 | —$C_2H_5$ | —$CH_3$ | —$CH_3$ | H | 4-Cl | 185–186 | 2 |
| 21 | —$CH_3$ | —$CH_3$ | —$CH_3$ | H | 2-Cl | 188 | 2 |
| 22 | —$CH_3$ | —$CH_3$ | —$CH_2$—C≡CH | H | H | 161 | 2 |
| 23 | —$C_2H_5$ | —$CH_3$ | —$CH_3$ | H | 2-$CH_3$ | 161–162 | 2 |

What is claimed is:

1. An 8-Aryl-5,6,7,8-tetrahydropyrazolo(3,4-b)(1,4)diazepine-1H,4H-5,7-dione of the formula

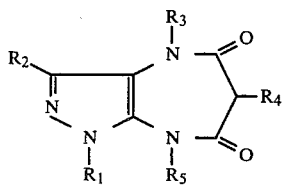

in which
  $R_1$ and $R_2$ are identical or different and represent each a hydrogen atom, an alkyl group having from 1 to 6 carbon atoms; or one of the radicals $R_1$ or $R_2$ may also be a benzyl or phenyl group;
  $R_3$ is a hydrogen atom, an alkyl group having from 1 to 6 carbon atoms; or an alkyl group substituted by an alkoxy group having from 1 to 6 carbon atoms, or a dialkylamino group having from 2 to 12 carbon atoms, or a cycloalkyl group having 3 to 6 carbon atoms; or an alkenyl or alkinyl group having from 2 to 6 carbon atoms; a cycloalkyl group having from 3 to 6 carbon atoms; or a carbalkoxy group having from 2 to 6 carbon atoms;
  $R_4$ is a hydrogen atom, an alkyl group having from 1 to 6 carbon atoms, a phenyl group, a hydroxy group an alkoxy group having from 1 to 6 carbon atoms, a carbalkoxy group having from 2 to 6 carbon atoms, an acyl group having from 2 to 6 carbon atoms, an amino group, an alkylamino group having from 1 to 7 carbon atoms or a dialkylamino group having from 2 to 12 carbon atoms, or a carbamoyl group, or a carbamoyl carrying on the amino group thereof an alkyl group having from 1 to 6 carbon atoms or a dialkyl group having from 2 to 12 carbon atoms;
  $R_5$ is a phenyl group, a phenyl group being mono- or bisubstituted by methyl, Cl, Br, F, nitro, cyano or trifluoromethyl, or a 2-pyridyl group.

2. The compound of claim 1 which is 1-Ethyl-3-methyl-8-phenyl-5,6,7,8-tetrahydropyrazolo(3,4-b)-(1,4)diazepine-1H,4H-5,7-dione.

3. The compound of claim 1, which is 1,3-dimethyl-8-phenyl-5,6,7,8-tetrahydropyrazolo(3,4-b)-(1,4)diazepine-1H,4H-5,7-dione.

4. An anxiolytic composition which comprises an effective amount of a compound as claimed in claim 1 in a unit dosage form from 1 mg/kg to 25 mg/kg of body weight of a host and a physiologically acceptable carrier therefor.

5. A method of treating a host suffering from anxiety which comprises orally administering to said host an effective dosage of about 5 to 50 mg/kg per day of a compound as defined in claim 1.

6. A method of treating a host suffering from anxiety which comprises intravenously administering to said host an effective dosage of from about 1 to 10 mg/kg per day of a compound as defined in claim 1.